(12) United States Patent
Berglund

(10) Patent No.: US 6,355,843 B1
(45) Date of Patent: Mar. 12, 2002

(54) PURIFICATION OF CARBOXALDEHYDE

(75) Inventor: Richard Alan Berglund, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/673,347

(22) PCT Filed: Mar. 15, 1999

(86) PCT No.: PCT/US99/05666

§ 371 Date: Oct. 10, 2000

§ 102(e) Date: Oct. 10, 2000

(87) PCT Pub. No.: WO99/57123

PCT Pub. Date: Nov. 11, 1999

Related U.S. Application Data

(60) Provisional application No. 60/084,299, filed on May 5, 1998.

(51) Int. Cl.⁷ ................................................ C07C 45/00
(52) U.S. Cl. ........................... 568/438; 568/425; 514/11
(58) Field of Search .................................. 568/425, 438; 514/11

(56) References Cited

U.S. PATENT DOCUMENTS

| 4,065,505 A | * 12/1977 | Kim et al. |
| 4,075,248 A | * 2/1978 | Marshall et al. |
| 4,162,269 A | * 7/1979 | Mizutani et al. |
| 5,840,684 A | * 11/1998 | Cooper et al. |

OTHER PUBLICATIONS

Allen et al, Synergic Aldehyd, Organic Synthesis Colle3ction, vol. 4, pp. 866, 1963.*

* cited by examiner

*Primary Examiner*—Gary Geist
*Assistant Examiner*—Hector M Reyes
(74) *Attorney, Agent, or Firm*—Tina M. Tucker

(57) ABSTRACT

The invention is directed to the process of purifying 4'-chloro-4-biphenylcarboxaldehyde.

10 Claims, No Drawings

PURIFICATION OF CARBOXALDEHYDE

This application is a 371 of PCT/US99/05666 filed Mar. 15, 1999 which claims benefit of Prov. No. 60/084,299 filed May 5, 1998.

This invention relates to the removal of impurities from 4'-chloro-4-biphenylcarboxaldehyde, a raw material used in the manufacture of $ND^{DISACC}$-4-(4-chlorophenyl) benzyl) A82846B, a glycopeptide antibiotic used to combat vancomycin resistant infections. A82846B is a fermentation product isolated from the culture broth of *Amycolatopsis orientalis*, which produces a mixture of closely related co-fermentation factors, A82846B being identified as the major antibacterial agent in the mixture. A82846B is reductively alkylated with 4'-chloro-4-biphenylcarboxaldehyde to form $ND^{DISACC}$-4-(4-chlorophenyl)benzyl) A82846B. By reducing the impurity level of the aldehyde raw material, there is seen an increase in overall yield, purity, and safety of the final antibiotic product.

The present invention provides an improved process for the removal of impurity from the synthesized 4'-chloro-4-biphenylcarboxaldehyde. The invention further provides a process for purifying 4'-chloro-4-biphenylcarboxaldehyde which comprises reacting 4'-chloro-4-biphenylcarboxaldehyde with sodium bisulfite in an aqueous/acetonitrile solution having an acetonitrile concentration sufficient to cause the bisulfite adduct to precipitate, isolating the bisulfite adduct precipitate from the solution, mixing the isolated bisulfite adduct in an aqueous/acetonitrile solution having a water concentration sufficient to cause the regenerated aldehyde to precipitate, and converting the bisulfite adduct to 4'-chloro-4-biphenylcarboxaldehyde.

The bisulfite adduct is represented by the formula:

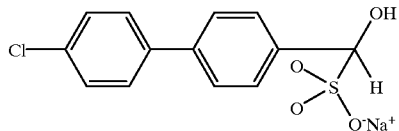

and shall be referred to herein as the bisulfite adduct.

This type of aldehyde purification is historically performed in an aqueous/alcohol solution, see Horning, E. C., *Organic Synthesis*, Collective Vol. 3, 438–440 (1955). Aqueous alcohol can be used as solvent in the present invention, but filtration of the novel bisulfite adduct and regenerated aldehyde is difficult and not commercially viable. In an improved embodiment of the present invention, aqueous acetonitrile is used. Use of this solvent allows better yields and purity of the purified aldehyde.

When reacting 4'-chloro-4-biphenylcarboxaldehyde with sodium bisulfite, the ratio of sodium bisulfite to 4'-chloro-4-biphenylcarboxaldehyde is not critical. The ratio can range from 1:1 to 10:1 sodium bisulfite to 4'-chloro-4-biphenylcarboxaldehyde. A preferred ratio for this reaction is from about 1:1 to about 1.3:1 sodium bisulfite to 4'-chloro-4-biphenylcarboxaldehyde. The solvent is not critical, so long as the bisulfite adduct precipitates. Aqueous methanol can be used, but aqueous acetonitrile has been found to be preferred. In this preferred embodiment, the ratio of acetonitrile to water during this reaction can range from about 2:1 to about 13:1 acetonitrile to water. A preferred range would be from about 5:1 to about 7:1 acetonitrile to water. The temperature for this reaction is not critical and can range from about 0° C. to about 100° C. The reactants are typically mixed at about 45° C. to about 55° C. and then cooled to about 15° C. to about 25° C.

When mixing the isolated bisulfite adduct in an solution and converting the bisulfite adduct to 4'-chloro-4-biphenylcarboxaldehyde, the solvent is not critical, so long as the regenerated aldehyde precipitates. Aqueous methanol can be used, but aqueous acetonitrile has been found to be preferred. In this preferred embodiment, the ratio of acetonitrile to water during this reaction can range from about 1:1 to about 1:5 acetonitrile to water. A preferred range would be from about 1:3 to about 1:5 acetonitrile to water. The reaction typically is done at ambient temperature from about 15° C. to about 25° C. The pH of the solution during the reaction can range either acidic, 0–3, or basic, 10–14. A preferred pH range would be from about 12 to about 14.

Examples 1 and 2 show a better yield of aldehyde when the conversion of bisulfite adduct to 4'-chloro-4-biphenylcarboxaldehyde is done in a aqueous/acetonitrile solution under basic conditions. Examples 2 and 3 monitor the impurity 4,4'-dichlorobiphenyl, referred to hereafter as 4,4'-DCBP, a polychlorinated biphenyl by definition. Example 3 shows a complete removal of 4,4'-DCBP in the aqueous/acetonitrile under basic conditions.

EXAMPLE 1

Preparation of Bisulfite Adduct of 4'-chloro-4-biphenylcarboxaldehyde 0.50 g of 4'-chloro-4-biphenylcarboxaldehyde was dissolved in 15 mL of methanol and 2 mL of water with heating. 0.30 g of sodium bisulfite was added and stirred for 10 min at 45–50° C. The solution was cooled to 0–5° C. and stirred for 1 hour. The bisulfite adduct precipitated and was filtered and washed with 5 mL methanol and then washed with 10 mL acetone. Yield was 97.1%.

(a) 0.15 g of the bisulfite adduct was stirred in 10 mL water, 5 mL methanol, and 2N hydrochloric acid was added to pH 2. The solution was heated slightly for 10 min. and stirred at room temperature for 20 min. A slurry was formed and the solid 4'-chloro-4-biphenylcarboxaldehyde filtered.

(b) 0.15 g of the bisulfite adduct was stirred in 10 mL water, 5 mL acetonitrile, and 5M sodium hydroxide was added to pH 12. The solution was stirred at room temperature for 20 min. A precipitate was formed and the solid 4'-chloro-4-biphenylcarboxaldehyde filtered.

The NMR spectra of the solids showed clean aldehyde from (b) and a 1.25:1 ratio of bisulfite adduct to aldehyde from (a).

EXAMPLE 2

Solvent and pH Comparisons

A 2.8 M solution of sodium bisulfite (1.2 equiv. relative to aldehyde) in water was added to a warm organic solution of 4'-chloro-4-biphenylcarboxaldehyde (0.46 M for acetone and acetonitrile, 0.28 M for alcohols). After cooling to ambient temperature and stirring 1h, filtration of the slurries afforded white solids which were analyzed for 4,4'-DCBP amounts. The conversion of the bisulfite adducts to aldehyde was then studied under either acidic (pH 0.9–1.1, HCl) or basic (pH 11–13, NaOH) conditions using the same organic solvents examined for derivative formation and a 2–2.2 h reaction time. The results are displayed in table 1. The data for the amount of bisulfite adduct remaining after attempted conversion was generated using $^1$H NMR integration of the spectra obtained from the isolated products. The original aldehyde samples used in this study contained 0.64% 4,4'-DCBP. ACN is abbreviated for acetonitrile, IPA is abbreviated for isopropyl alcohol, and 3A alc is abbreviated for 3A alcohol.

TABLE 1

| Solvent | 4,4'-DCBP in adduct | Bisulfite Adduct Remaining (%) | | Aldehyde Yield (%) | | 4,4'-DCBP in Recovered Aldehyde | |
|---|---|---|---|---|---|---|---|
| | | HCl | NaOH | HCl | NaOH | HCl | NaOH |
| acetone | 50 ppm | 18 | 0 | 80.0 | 88.5 | 70 ppm | 80 ppm |
| methanol | 100 ppm | 88 | 17 | 16.3 | 90.7 | 70 ppm | 100 ppm |
| ACN | ND | 93 | 0 | 8.8 | 93.2 | ND | ND |
| 3A alc | ND | 94 | 16 | 8.1 | 92.4 | ND | ND |
| IPA | ND | 94 | 7.7 | 8.0 | 86.0 | ND | ND |

*ND-not detected at a detection limit of 50 ppm.

EXAMPLE 3

Optimization of Conversion of Aldehyde to Bisulfite Adduct

Variables examined during the optimization of example 2 are concentration of aldehyde in acetonitrile, concentration of sodium bisulfite in water, and reaction time. Yield of dried bisulfite adduct and amount of residual 4,4'-DCBP were evaluated. The results are summarized in table 2. The original aldehyde samples used in this study contained 0.64% 4,4'-DCBP.

TABLE 2

| Series | Ald. Conc (M) | NaHSO$_3$ Conc. (M) | ACN:H$_2$O | Time (h) | Yield of bisulfite adduct (g) | 4,4'-DCBP (ppm) |
|---|---|---|---|---|---|---|
| A | 0.38 | 1.7 | 3.8 | 2 | 6.9 | ND |
| B | 0.31 | 2.3 | 6.7 | 3 | 6.8 | ND |
| C | 0.23 | 3.5 | 12.5 | 4 | 6.3 | 465 |
| D | 0.31 | 2.3 | 6.7 | 3 | 7.4 | ND |
| E | 0.38 | 3.5 | 3.8 | 4 | 6.5 | 339 |
| F | 0.38 | 3.5 | 3.8 | 2 | 5.5 | 235 |
| G | 0.31 | 2.3 | 6.7 | 3 | 6.7 | ND |
| H | 0.23 | 1.7 | 6.3 | 2 | 7.1 | ND |
| I | 0.23 | 3.5 | 12.5 | 2 | 7.7 | ND |
| J | 0.38 | 1.7 | 3.8 | 4 | 7.2 | ND |
| K | 0.23 | 1.7 | 6.3 | 4 | 7.4 | ND |

*ND-not detected at a detection limit of 30 ppm, each run used 5 g aldehyde.

The study identifies overall concentration as a significant factor relating to the removal of 4,4'-DCBP. The more concentrated reactions, E and F, were not efficient for the 4,4'-DCBP removal. A final observation is that the filterability of the bisulfite adducts decreased as the ratio of acetonitrile to water was reduced.

EXAMPLE 4

Study of the Conversion of Bisulfite to Aldehyde

A large sample of bisulfite adduct, free of 4,4'-DCBP, was prepared and a comparison of water amount, acetonitrile amount, and ambient temperature reaction time was performed. Parameters evaluated were yield and filterability (+ refers to efficient filtration, − refers to poorly filtering material). For each trial, bisulfite adduct (4 g) was stirred in a mixture of water and acetonitrile. A 50% sodium hydroxide solution was added to adjust the pH to 12. The study results are summarized in table 3.

TABLE 3

| Series | H$_2$O (mL) | ACN (mL) | H$_2$O:ACN | Conc. (M) | Time (h) | Yield (%) | Filterability |
|---|---|---|---|---|---|---|---|
| A | 25 | 10 | 2.5 | 0.35 | 1 | 90.0 | + |
| B | 25 | 10 | 2.5 | 0.35 | 3 | 90.3 | + |
| C | 25 | 20 | 1.25 | 0.28 | 1 | 82.0 | + |
| D | 25 | 20 | 1.25 | 0.28 | 3 | 81.3 | + |
| E | 45 | 10 | 4.5 | 0.23 | 1 | 92.4 | − |
| F | 45 | 10 | 4.5 | 0.23 | 3 | 92.3 | − |
| G | 45 | 20 | 2.25 | 0.19 | 1 | 91.0 | − |
| H | 45 | 20 | 2.25 | 0.19 | 3 | 91.5 | − |
| I | 35 | 15 | 2.33 | 0.25 | 2 | 91.7 | + |
| J | 35 | 15 | 2.33 | 0.25 | 2 | 91.4 | + |
| K | 35 | 15 | 2.33 | 0.25 | 2 | 90.3 | + |

The study demonstrates that a relatively high water to acetonitrile ratio is important for high aldehyde yield. In addition, the most dilute reactions result in poor aldehyde filterability.

EXAMPLE 5

Aldehyde Clean-up: Removal of Impurities

Aldehyde Clean-up Conditions:
1. Adduct Formation
   a. 0.23 M aldehyde solution
   b. 1.7 M bisulfite solution (1.2 molar equivalents bisulfite relative to aldehyde)
   c. Reaction time to be monitored by NMR analysis of removed aliquots
   d. High Volume ACN wet cake wash
2. Conversion of adduct to aldehyde
   a. 0.28 M concentration for the bisulfite adduct
   b. 4:1, water to ACN ratio
   c. 2 hour reaction time at pH 12–14, verify by
   NMR Analysis of Removed Aliquots The experiment began with 25 kg of 4'-chloro-4-biphenylcarboxaldehyde. No 4,4'-DCBP was detected in the purified aldehyde, and the total amount of related substance impurities was reduced from 0.9% to 0.3%. The yield of purified aldehyde was 22.2 kg (89%) purified aldehyde.

I claim:

1. A process for preparing a bisulfate adduct of 4'-chloro-4-biphenylcarboxaldehyde, comprising: reacting 4'-chloro-4-biphenylcarboxaldehyde with sodium bisulfite to obtain the bisulfite adduct, wherein the reaction is conducted in an aqueous acetonitrile solution having an acetonitrile concentration sufficient to cause the bisulfite adduct to precipitate.

2. The process of claim 1, wherein the ratio of acetonitrile to water is from about 2:1 to about 13:1.

3. A process for purifying 4'-chloro-4-biphenylcarboxaldehyde which comprises:

(1) reacting 4'-chloro-4-biphenylcarboxaldehyde with sodium bisulfite in an aqueous/acetonitrile solution having an acetonitrile concentration sufficient to cause the bisulfite adduct to precipitate, (2) isolating the bisulfite adduct precipitate from the solution, (3) mixing the isolated bisulfite adduct in an aqueous/acetonitrile solution having a water concentration sufficient to cause the regenerated aldehyde to precipitate, and (4) converting the bisulfite adduct to 4'-chloro-4-biphenylcarboxaldehyde.

4. A compound of the formula:

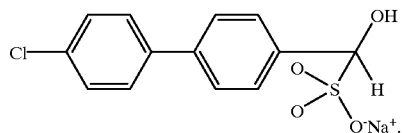

5. A process for preparing a bisulfate adduct of 4'-chloro-4-biphenylcarboxaldehyde, comprising:
  (1) reacting 4'-chloro-4-biphenylcarboxaldehyde with sodium bisulfite in an aqueous acetonitrile solution having an acetonitrile concentration sufficient to cause the bisulfite adduct to precipitate; and
  (2) isolating the bisulfite adduct precipitate from the solution.

6. The process of claim 5, wherein the ratio of acetonitrile to water in step (1) is from about 2:1 to about 13:1.

7. The process of claim 3, wherein the ratio of acetonitrile to water in step (1) is from about 2:1 to about 13:1.

8. The process of claim 3, wherein the ratio of acetonitrile to water of the solution in step (3) is from about 1:3 to about 1:5.

9. The process of claim 3, wherein the pH of the solution in step (3) is from about 12 to about 14.

10. The process of claim 9, wherein the pH of the solution in step (3) is from about 10 to about 14.

\* \* \* \* \*

UNITED STATES PATENT AND TRADEMARK OFFICE
CERTIFICATE OF CORRECTION

PATENT NO. : 6,355,843 B1  
DATED : March 12, 2002  
INVENTOR(S) : Berglund

It is certified that error appears in the above-identified patent and that said Letters Patent is hereby corrected as shown below:

Column 4,  
Line 45, "bisulfate adduct" should read -- bisulfite adduct --

Column 5,  
Line 10, "bisulfate adduct" should read -- bisulfite adduct --

Signed and Sealed this

Twenty-fourth Day of May, 2005

JON W. DUDAS  
*Director of the United States Patent and Trademark Office*